United States Patent [19]

Hanley et al.

[11] 4,180,091
[45] Dec. 25, 1979

[54] PURGING MEANS FOR APERTURE OF BLOOD CELL COUNTER

[75] Inventors: John P. Hanley, West Paterson; Pasquale M. Petrucci, Morristown; Stanley Pfeifer, Mendham, all of N.J.

[73] Assignee: Becton, Dickinson and Company, East Rutherford, N.J.

[21] Appl. No.: 852,953

[22] Filed: Nov. 18, 1977

[51] Int. Cl.² .............................. G01N 27/00
[52] U.S. Cl. ...................... 137/238; 134/102; 134/169 C; 324/71 CP
[58] Field of Search .................... 324/71 CP; 137/238–241; 134/102, 169 C

[56] References Cited

U.S. PATENT DOCUMENTS

| | | | |
|---|---|---|---|
| 3,259,891 | 7/1966 | Coulter et al. | 137/240 X |
| 3,746,976 | 7/1973 | Hogg | 324/71 CP |
| 3,783,376 | 1/1974 | Doniguian | 324/71 CP |

OTHER PUBLICATIONS

H. E. Kubitschek, *Apertures for Coulter Counters*, in Review of Scientific Instruments, vol. 35, No. 11, pp. 1598–1599, Nov. 1964.

*Primary Examiner*—Martin P. Schwadron
*Assistant Examiner*—Richard Gerard
*Attorney, Agent, or Firm*—Kane, Dalsimer, Kane, Sullivan and Kurucz

[57] ABSTRACT

A system for purging the aperture and surrounding portions of a blood cell counter of dirt, debris, and previous sample liquid. A sample tube extends from a source of either sample liquid or cleansing solution to a small gap between the aperture and housing assembly. A purge line is connected between an annular portion surrounding the gap and a pump which supplies negative pressure. Due to the geometry of the sample tube, gap, annulus, and purge line, a high pressure drop occurs across the gap and the liquid flows at relatively high velocity past the aperture to facilitate cleaning.

10 Claims, 5 Drawing Figures

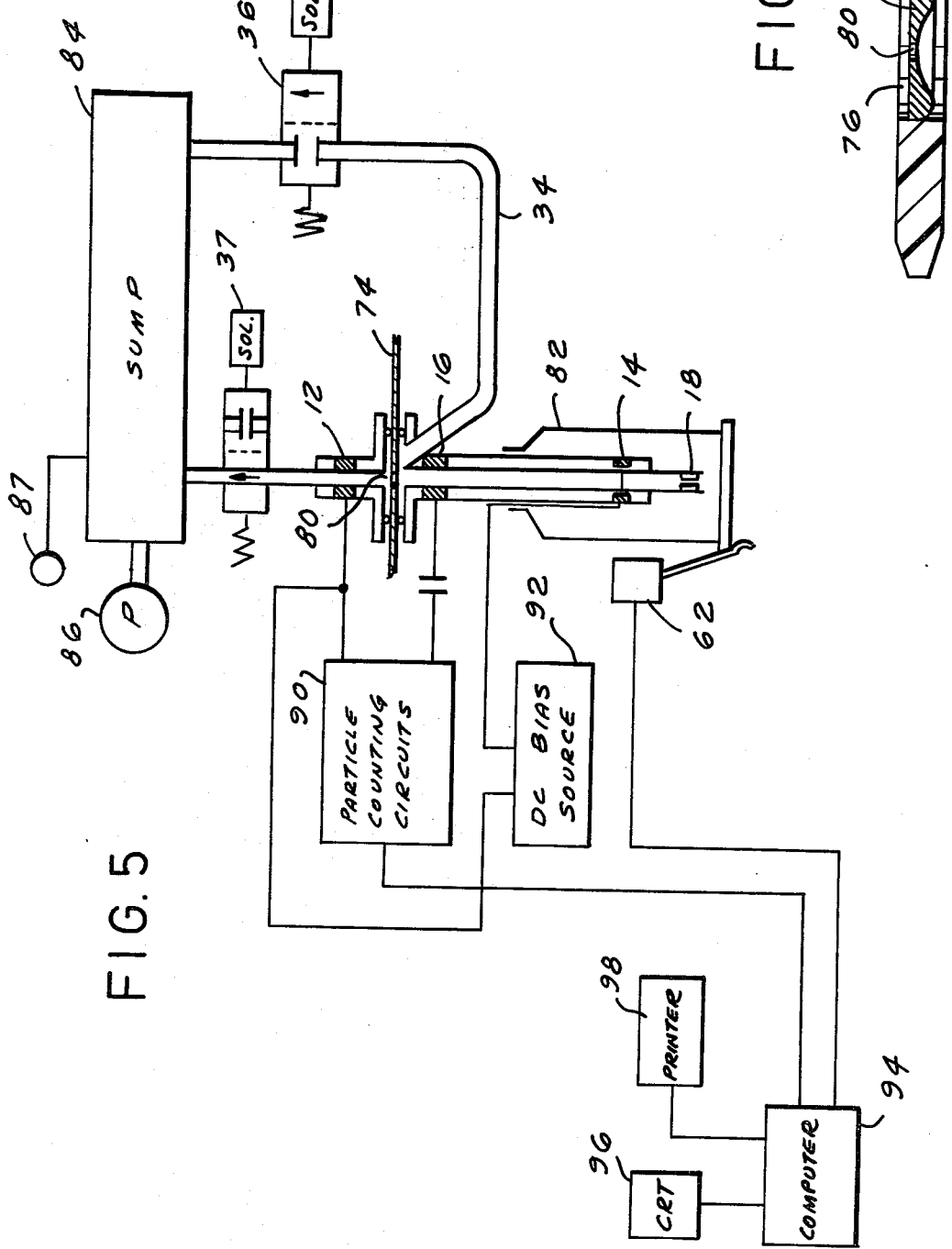

PURGING MEANS FOR APERTURE OF BLOOD CELL COUNTER

BACKGROUND OF THE INVENTION

The invention relates to the field of purging systems for blood cell counters, particularly those having sensing zones including apertures of small dimensions.

There are presently a number of methods for clearing debris which accumulates about the aperture of a blood cell counter. One method involves providing a cleansing solution in the instrument in place of the sample solution, and running it through the system as one would during the counting operation. This is fairly effective, but sufficient velocity of the cleansing stream may not be generated about the aperture to remove all debris, and the process is time consuming. An additional problem is that the debris may be too large to pass through the aperture.

Another method involves either the physical displacement or "flicking" of the aperture slide as described in commonly assigned U.S. Pat. No. 3,783,376.

Independent purging systems have also been employed where the previous sample is removed by a separate purge line rather than through the fluidic circuit normally used for counting. A system which develops sufficient velocity in the area about the aperture to most effectively remove dirt and debris which could clog it has not previously been developed.

SUMMARY OF THE INVENTION

The invention relates to blood cell counters and, in particular, to devices for counting cells suspended in a fluid medium of substantially different conductivity. A purge system is provided which may be advantageously utilized in the system as described in a commonly assigned application entitled "Blood Cell Counter Having Three-Electrode Counting Head," Ser. No. 833,559 filed Sept. 15, 1977.

The invention is applied to counting systems wherein a suspension of blood cells or platelets is passed through an aperture of selected dimensions, thereby abruptly increasing the resistance across the aperture. A DC signal is applied to electrodes on each side of the aperture, and the signal is modulated by the variation of the resistance between sensing electrodes. A detector senses the electronic pulses produced in this manner, and appropriate electronic circuitry processes the signals to produce a cell count or hematocrit determination. The latter process is described in detail in U.S. Pat. No. 3,812,425. A pulse processing and counting circuitry is particularly described in U.S. Pat. No. 3,973,194.

The present invention is described in terms of a transducer assembly having at least three electrodes for (1) producing a DC signal which passes through the aperture and (2) sensing the pulses produced as the poor-conducting blood cells pass through the aperture. The electrodes are of such structure and configuration so as to minimize the number of bubbles passing through the aperture, and to minimize the effect of the diluent in the path between the biasing electrodes and the aperture.

First and second electrodes are provided on opposite sides of the aperture, and a DC bias source is connected between them. A diluted blood sample is drawn through the aperture in the direction of the first electrode, and pulses are generated by a detector circuit as blood cells pass through. This blood cell detection circuitry is connected between a third electrode, located between the aperture and the second electrode, and the first electrode. The second electrode is located externally of the channel which leads to the aperture. Any bubbles formed on this electrode are therefore outside of the detection system and cannot enter the aperture. Instead of rising through the channel and into the aperture, they reach the surface of the diluted sample within a reservoir where they enter the atmosphere.

The length of the third electrode and magnitude of the bias current are arranged to maintain the voltage drop across the electrode length such that bubbles are not generated from the third electrode, in an amount sufficient to impair operation of the apparatus.

The third electrode is located in close proximity to the aperture to increase the sensitivity of the apparatus and minimize the effects of any changes in the diluent resistance. Because the sample tube through which the diluted sample flows has a small diameter to reduce carryover, there is considerable resistance between the second electrode and the aperture. By locating the third electrode near the aperture, any adverse effects of the resistant path between the second and third electrode are eliminated.

The path from the third electrode to the detection circuit has high DC impedance to prevent this electrode from becoming a bubble generator.

Although described in terms of this particular transducer, the novel purge system would be equally applicable to other transducers which include an aperture of small dimensions such as provided in this embodiment.

The purge flow manifold assembly includes a fluidic circuit which is designed to maximize the cleansing effect in the area of the aperture through which the blood particles pass. In this manner, debris clogging of the aperture is cleared away and previous sample is removed from the transducer. A sample tube extends from a source of diluted blood sample or a cleansing agent to within a short distance of the aperture slide. An annulus surrounds the lower portion of the slide area and aperture, and a purge line is in fluid communication with the annulus. When a source of vacuum is applied to the purge line, a relatively high-velocity fluid stream is directed past the jeweled aperture due to the small gap provided between the slide and the sample tube and transducer housing assembly. The annulus is relatively large compared to this small purge flow gap, and promotes symmetrical bathing of the jewel. In this manner, previous sample and debris are effectively removed from the transducer.

It is among the primary objects of the invention to provide a purge system for a blood cell counter which will most quickly and effectively remove debris which tends to clog the aperture within the transducer head.

It is another object of the invention to provide a system for removing previous sample from the transducer so that accurate cell counts may be obtained.

Other objects and advantages of the invention will become apparent from the detailed description which follows.

DESCRIPTION OF THE DRAWINGS

FIG. 4 is a sectional view of the jeweled aperture slide which is inserted into the counting head.

FIG. 5 is a view of the invention as incorporated within a blood cell counting instrument.

DESCRIPTION OF THE INVENTION

Although the invention is described in terms of a blood cell counter, it should be understood that blood cells will include platelets and other blood particles for the purposes of this application.

Figure 1:
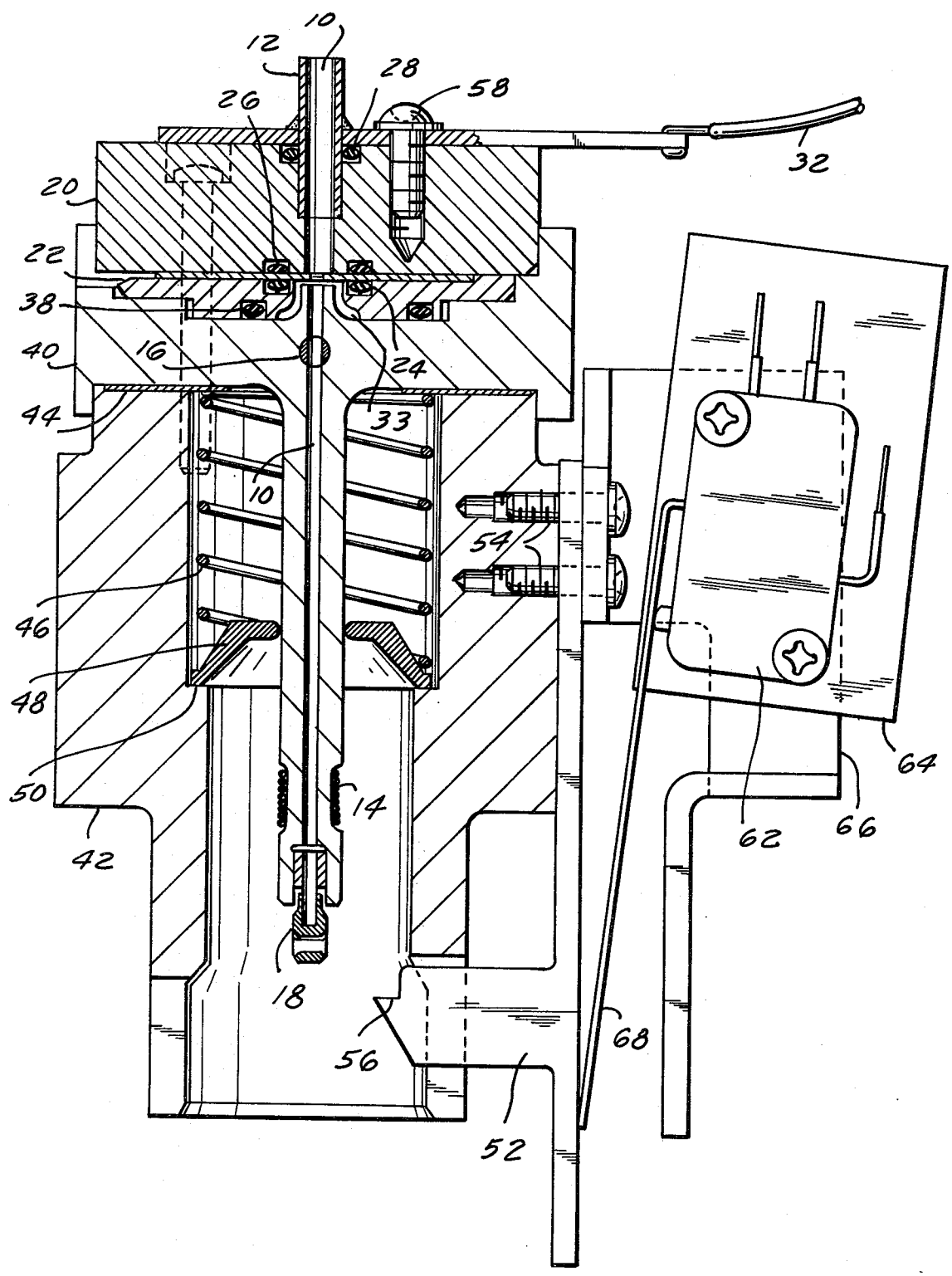
FIG. 1 is a sectional view of the head and transducer assembly.

FIG. 1 illustrates the invention in detail including the aperture slide which is inserted when the instrument is in use, but excluding the reservoir containing the sample which is to be in fluid communication with the aspirating tube.

A non-metallic conduit 10 is provided through which the diluted blood sample will flow. Three electrodes, 12, 14, and 16 are located along this conduit. The lower electrode 14, is positioned outside conduit 10. The conduit 10 may be considered to be two conduits, each aligned with the other and having a terminal end near the aperture slide. A filter 18 is included at the lower end of the conduit.

An aperture slide as shown in FIG. 4 is designed to fit between the upper housing 20 of the transducer, and the housing 22 which includes the assembly for purging the system of debris which may clog the aperture. "O" rings 24 and 26 insure the leakproof insertion of the slide, and provision is made so that the jeweled aperture will be positioned within the conduit 10. The aperture is described in more detail in commonly assigned U.S. Pat. No. 3,783,376. Upper housing 20 and upper electrode 12 are interfaced by an O-ring 28 at the point where plate 30 is secured to this electrode. Wire 32 leads from plate 30, and is connected to circuitry which will later be described.

Figure 2:
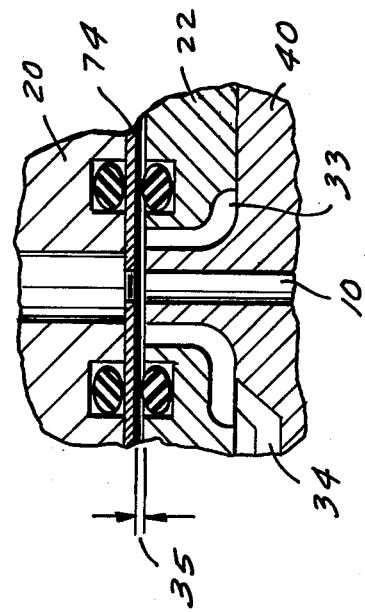
FIG. 2 is an enlargement of the area near the aperture as shown in FIG. 1, taken along the section line 2—2 of FIG. 3.

The purge assembly, which is more clearly shown in FIG. 2, includes housing 22, conduit 34, annulus 33, and solenoid valves 36 and 37. The dimensions of the sample tube 10, annulus 33 and vacuum purge line 34 are seen to be relatively large in comparison to the purge flow gap 35. In a successful application of this invention, the purge flow gap 35 is 0.002 to 0.012" between slide 74 and housing 40. "O" ring 38 is positioned between the purging housing 22 and housing 40. Electrodes 14 and 16 are within housing 40, which is separated from base 42 by a gasket 44. Base 42 contains a spring 46 which is held by a retainer 48 against a protrusion 50. A latch 52 is also secured to the base by bolts 54. The latch has a protrusion 56 upon which the base of a sample reservoir may rest.

A number of bolts, as shown at 58, and screw 60, are used to maintain the structure of the transducer assembly, which is comprised of the several housing and other components described above.

A reservoir position detecting switch 62 is also secured to the transducer assembly. An insulator 64 separates the switch from bracket 66. The switch includes a mounting bracket 66, an actuating lever 68, and button 69.

Figure 3:
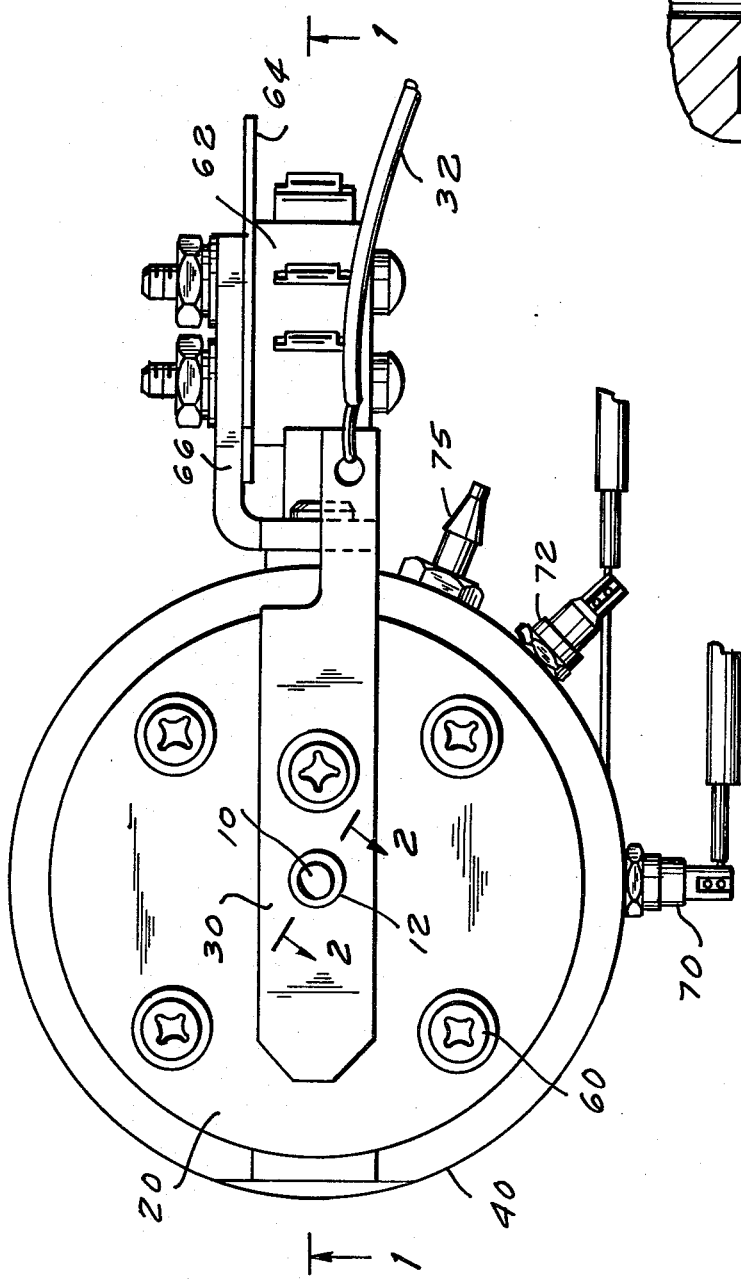
FIG. 3 is a top view of the counting head and transducer assembly.

Referring to FIG. 3, a top view of the transducer is shown. Terminals 70 and 72 connect electrodes 16 and 14 to the appropriate circuitry, and a fitting 75 is shown for attachment of the purge line 34. Annulus 33 (FIG. 2) is in fluid communication with both the sample tube 10 and the purge line 34.

The aperture slide 74, as shown in FIG. 4, is inserted between housing assembly 22 and upper housing 20 before the counting procedure can begin. O-rings 24 and 26 provide a leakproof seal when the slide is in position. The slide is formed of a polyester film such as Mylar, having a thickness of approximately 0.014 inch and a length of approximately 2 inches. However, any suitable material may be used. A hole 76 is formed near one end of the aperture slide and positioned to be aligned with tube 10. The forward edge is beveled to facilitate its insertion. A jewel 78, preferably a ruby, is press fit into hole 76. The jewel has a thickness of about 0.25 mm and an outside diameter of approximately 1.20 mm. An aperture 80 is formed in the jewel, and in this embodiment has a diameter of 70 microns.

FIG. 5 illustrates the basic invention as applied to a simplified counting system. The lower end of the conduit 10 is immersed in a diluted blood sample contained within a reservoir 82. A sump 84 is in fluid communication with the conduit, and a pump 86 and regulator 87 maintain the vacuum which is exerted on the system through tube 88 and sump 84. As can most clearly be seen in this figure, the counting circuitry 90 is connected between electrodes 12 and 16, and the DC bias source 92 between electrodes 12 and 14. The counting circuits are connected to a microcomputer 94 which performs calculations using the data received to generate all parameters at the end of the test. Test results are displayed by either cathode ray tube display 96 or printer 98, although any conventional device such as a meter can also be employed. The pulses may be processed in the manner described in copending application entitled "Method and Apparatus For Providing Accurate Blood Cell Counts," Ser. No. 833,558 filed Sept. 15, 1977.

The electrodes and their connections are shown in FIG. 5. The lower electrode 14 is located outside the sample tube 10 in such a manner that bubbles generated by electrolysis exit from the surface of the diluted sample within the reservoir 82. These bubbles will not enter the sample tube where they could then flow through the aperture 80 and impair the system.

The DC bias source 92 is connected to electrodes 14 and 12. Bubbles formed at electrode 12 will rise harmlessly above the sensing zone between electrodes 16 and 12.

Electrodes 16 and 12 are connected to the detecting/counting circuits 90, and aperture 80 is located between these electrodes. It is therefore of utmost importance that a minimum of bubbles is generated at electrode 16, as these bubbles would flow directly into aperture 80 thereby clogging it or causing errors within the detection system. It is also important that electrodes 16 and 12 are located near the aperture to minimize the effects of any variance in the resistance of the dilution. Because the detector is not always able to distinguish pulses caused by varying resistance of the diluent from those caused by the passage of a pulse through the aperture, keeping the distance between the detection electrodes small is necessary.

The sensitivity of the device is also improved by keeping the distance between the sensing electrodes small. The resistance of the liquid in the sample tube is typically about 25 Kohms in this embodiment, whereas the resistance of the aperture is about 20 Kohms. By placing electrodes 12 and 16 in close proximity to the aperture, the effects of the 25 Kohm segment is eliminated. Instead of detecting a resistance change caused by a blood cell with respect to a total resistance of 45 Kohms in the system, this change is measured with respect to only 20 Kohms. Although the resistance within the tube could be greatly diminished by use of a larger diameter sample tube, the small tube is desirable to reduce carryover. In a successful application of this invention, tube 10 has a diameter of approximately 0.05".

Bubble generation caused by electrolysis of electrode 16 is minimized or eliminated by two features of the invention. First, the detection circuitry is connected such that significant current is not drawn from the electrode. A high impedance return path to the circuitry is therefore provided. Secondly, the length of the electrode 16 in the diluent path and the magnitude of the DC bias current are arranged to minimize the voltage drop across the electrode length.

The resistance R of a uniform conductor is defined by the expression $R=\rho(l/A)$, where l is its length, A is its cross-sectional area, and $\rho$ is its resistivity. In this successful embodiment, the length of the electrode 16 is 0.095 inches, the diameter of the sample tube is 0.07 inches, and the resistivity of the dilution is about 20 ohm-inches. Applying the above formula, the resistance is found to be 494 ohms. The voltage drop V is defined by the formula $V=IR$, and for a 1 ma DC current, the voltage drop is 0.494 volts. It should be understood that other tube diameters, electrode lengths, and biasing currents may be utilized in providing a voltage drop of less than about 1.2 volts. 1.2 volts has been found to be a good target figure, although this particular voltage is not to be regarded as critical.

To begin the testing procedure, reservoir 82 is positioned against retainer 48 so as to compress spring 46. The spring is compressed until the reservoir bottom rests against the protrusion 56 provided on latch 52. Switch 62 provides information to the computer as to whether the reservoir is inserted. Actuation lever 68 presses button 69 to actuate the switch once the reservoir is in place.

The reservoir 82 is positioned such that the sample may be aspirated through filter 18, conduit 10, aperture 80, circuit 10, and into sump 84. The pump operates to provide the negative pressure necessary for the aspiration.

As the sample is aspirated through the conduits and electrodes, the blood cells are counted in a conventional manner based upon the change in current between the detection electrodes each time a blood cell enters the aperture. Pulses are produced and counting circuitry 90 counts the number of blood cells. This information is relayed to computer 94 which causes printer 98 to record the results and/or cathode ray tube display 96 to visually display the information. The counting process is described in greater detail in U.S. Pat. Nos. 3,812,425 and 3,973,194, as are the basic circuit components.

Before the next sample is aspirated through the electrodes to commence the counting procedure, the sample presently within the transducer between the filter 18 and aperture slide 74 is removed. This is accomplished by actuation of pump 86, which provides a source of vacuum pressure, and the opening of a solenoid valve 36 on the purge line such that fluid flows through this line into the sump 84.

The purge system basically includes the pump 86 for supplying negative pressure, the sump 84 which temporarily stores liquid drawn into it, the conduit connecting the sump with the transducer assembly, and the novel fluidic circuit within the transducer. This circuit includes the relatively large sample tube 10, the small gap 35 between the aperture slide 74 and the housing 40, the relatively large annulus 33 which surrounds the lower portion of the slide, and the relatively large diameter purge line 34.

The pump 86 supplies the negative pressure for the system, and purging is accomplished upon the closing of valve 37 and opening of valve 36. A total pressure drop $\Delta P_T$ must occur between the bottom of sample tube 10 and the pump. It is one of the primary objectives of the invention to obtain the greatest proportion of this drop across the gap 35 between the slide and housing. The pressure drop across the gap will be referred to as $\Delta P_G$, so it is the ratio of $\Delta P_G/\Delta P_T$ that will be maintained as high as possible. This is accomplished by providing system components which minimize pressure drop throughout the remainder of the system. By maintaining a $\Delta P_G$ as high as possible, the velocity of the liquid is significantly increased in the gap area. Because a high velocity stream is directed across the slide in the area near the aperture, debris within or near the aperture is most effectively cleared away.

To obtain the aforementioned advantages of a relatively high velocity stream near the aperture, the sample tube, annulus, and purge line are all of such dimensions that fluid velocity will be relatively slow within them, and the pressure drop is minimized. All have larger dimensions than the gap as clearly shown in FIGS. 2 and 5. Losses due to frictional forces and turbulence are accordingly reduced. The gap is shown to be of relatively small dimensions, and a correspondingly high drop in pressure is produced. Due to this drop, the liquid velocity increases in this area thus enhancing its cleansing action near the aperture.

Another advantageous feature of the purge system is the provision of the annular cavity 33 which surrounds the gap. As shown in FIG. 1, the annulus appears to be symmetrical. The view shown in FIG. 2 indicates there is actually a lobed portion near its junction with purge line 34. In practice, the annulus may be either symmetrical or lobed, and there are advantages in both designs.

The annulus is provided for the basic purpose of insuring a uniform flow about the jewel. If no such area surrounded the gap, liquid would tend to flow directly to whichever side the purge line was attached. Consequently, dirt or debris on the opposite side of the jewel might not be effectively removed. By providing an annulus or other open area of relatively large dimensions surrounding the gap, a fountain-like flow from the top of the tube 10 occurs across the face of the jewel.

If the annulus is symmetrical, the flow is uniform in nearly all radial directions. The pressure drop within the annulus itself is also minimized with such a configuration.

Rather than being completely symmetrical, the annulus which is most clearly shown in FIG. 2 indicates that it contains a lobed portion. This reduces the volume of the annular region as compared with a symmetrical annulus extending to the outer periphery of the lobe. Although the uniformity of flow from the sample tube is somewhat impaired, there is still sufficient high velocity flow in all radial directions to insure effective cleaning of the jewel. The reduced volume of this configuration is advantageous in that it minimizes the area in which air may be trapped. As previously explained, air bubbles within the aperture are undesirable. A further advantage of the smaller annulus occurs when a hemoglobin head (not shown) is located along the purge line, such as shown in commonly assigned application Ser. No. 833,560, filed Sept. 15, 1977. There is reduced carry-over of previous sample, and less new sample is thereby required to flush the system before performing a new test.

It should be understood that although the invention has been described as applied to a particular transducer, the same concept can be applied to any other transducer having an aperture which should be flushed.

The above description and drawings are intended to be illustrative and not limiting, and the scope of the invention to be determined in light of the appended claims.

What is claimed is:

1. A purge system for a blood cell counter of the type including a support structure with an aperture therein positioned between sensing electrodes which detect the passage of a cell through said aperture, comprising:
    a housing assembly;
    a first conduit within said housing assembly having a downstream end terminating at an outer wall thereof;
    an aperture and supporting structure therefor positioned near said downstream end of said first conduit, there being a gap defined between said supporting structure and said outer wall of said housing assembly, said aperture and said gap being in fluid communication with each other;
    a second conduit in fluid communication with said gap such that a fluid is able to flow radially outwardly from said first conduit, through said gap, and into said second conduit, said first conduit and said second conduit both having relatively large cross-sectional areas in comparison with that of said gap such that the pressure drop per unit length of a liquid flowing through said conduits is less than the pressure drop per unit length of a liquid flowing through said gap;
    a third conduit having an end terminating near said aperture and in fluid communication therewith, said terminal end of said third conduit positioned on the opposite side of said aperture and said support structure from said first conduit and adapted to receive liquid flowing through said aperture; and
    means for applying negative pressure to said second conduit,
    whereby a relatively high velocity liquid stream may be provided within said gap and adjacent the upstream side of said aperture when negative pressure is applied to said second conduit, said stream being able to effectively flush debris into said second conduit.

2. A system as described in claim 1 wherein the gap is between 0.002 and 0.012 inches.

3. A system as described in claim 1 wherein the first conduit has a diameter of about 0.05 inches.

4. A system as described in claim 1 wherein the means for applying negative pressure to the second conduit is a pump.

5. A system as described in claim 4 wherein a sump is provided between the pump and the second conduit.

6. A system as described in claim 1 wherein the supporting structure for the aperture is a slide having a jewel with an aperture formed therein.

7. A system as described in claim 1 wherein a substantially annular cavity is provided within said housing assembly, said annular cavity being in fluid communication with and surrounding said gap and in fluid communication with said second conduit such that liquid may flow from said first conduit through said gap, into said annular cavity, and then to said second conduit, said liquid being able to flow in substantially all radial directions through said gap upon the application of negative pressure to said second conduit.

8. A system as described in claim 7 wherein said annular cavity is lobed in one direction.

9. A system as described in claim 7 wherein said annular cavity is designed so as to minimize the pressure drop of a liquid flowing therethrough.

10. A system as described in claim 1 wherein said first conduit, said third conduit and said aperture are aligned with each other, the second conduit being positioned radially outwardly from said first conduit.

* * * * *